(12) United States Patent
Toth

(10) Patent No.: US 7,101,078 B1
(45) Date of Patent: Sep. 5, 2006

(54) METHODS AND SYSTEMS FOR IMAGING SYSTEM RADIATION SOURCE ALIGNMENT

(75) Inventor: Thomas Louis Toth, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/056,310

(22) Filed: Feb. 11, 2005

(51) Int. Cl.
*A61B 6/08* (2006.01)
(52) U.S. Cl. ......................................... 378/205; 378/19
(58) Field of Classification Search ................... 378/4, 378/19, 205
See application file for complete search history.

(56) References Cited

U.S. PATENT DOCUMENTS

| | | | |
|---|---|---|---|
| 5,469,429 A | 11/1995 | Yamazaki et al. ............. | 378/19 |
| 5,550,889 A | 8/1996 | Gard et al. .................. | 378/113 |
| 6,056,437 A * | 5/2000 | Toth ............................ | 378/205 |
| 6,359,958 B1 * | 3/2002 | Toth ............................. | 378/19 |

* cited by examiner

*Primary Examiner*—Courtney Thomas
(74) *Attorney, Agent, or Firm*—Carl B. Horton, Esq.; Armstrong Teasdale LLP

(57) ABSTRACT

Methods and systems for aligning an x-ray source position in an imaging system are provided. The imaging system includes a multislice detector array having a plurality of rows of detector cells displaced along a z-axis and an x-ray source for radiating an x-ray beam toward the detector array. The system is configured to determine an x-ray beam z-axis profile using the detector array, and determine an adjustment to the position of the x-ray source based on the determined x-ray beam z-axis profile.

23 Claims, 4 Drawing Sheets

METHODS AND SYSTEMS FOR IMAGING SYSTEM RADIATION SOURCE ALIGNMENT

BACKGROUND OF THE INVENTION

This invention relates generally to computed tomography (CT) imaging and more particularly, to alignment of a radiation source in a CT imaging system.

In at least one known CT imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reducing scan time, helical scanning provides other advantages such as better use of injected contrast, improved image reconstruction at arbitrary locations, and better three-dimensional images.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical weighting scheme, the projection data can be "weighted" prior to filtered back projection. Thus, one technical effect is the generation of a volumetric CT three-dimensional (3D) image of a scanned object.

Multislice CT systems are used to obtain data for an increased number of slices during a scan. Known multislice systems typically include detectors generally known as 3-D detectors. With such 3-D detectors, a plurality of detector elements form separate channels arranged in columns and rows. Each row of detectors forms a separate slice. For example, a two-slice detector has two rows of detector elements, and a four-slice detector has four rows of detector elements. During a multislice scan, multiple rows of detector cells are simultaneously impinged by the x-ray beam, and therefore data for several slices is obtained.

The image reconstruction process relies on a very accurately positioned focal spot from which the fan-shaped x-ray beam is emitted. The focal spot is the location on the x-ray tube anode that is struck by an electron beam emanating from a cathode. Misalignment of this focal spot may result in sampling errors that reduce image resolution and produce image artifacts.

Perfect mechanical alignment of the x-ray tube focal spot is difficult to achieve in a commercial production setting and difficult to maintain in a clinical setting. Calibration and alignment procedures are used to position the x-ray tube focal spot during initial manufacture. These procedures are delicate and time consuming. However, if a detector tube fails after the scanner has been in operation, a new tube must be installed and aligned. In such a case, because of new build dimensional tolerances and/or previous detector calibration procedures being performed, the collimator and detector are assumed to be in proper alignment and only the position of the new tube ($Z_c$) needs to be adjusted.

BRIEF DESCRIPTION OF THE INVENTION

In one embodiment, a system for aligning an x-ray source position in an imaging system is provided. The imaging system includes a multislice detector array having a plurality of rows of detector cells displaced along a z-axis and an x-ray source for radiating an x-ray beam toward the detector array, wherein the system is configured to determine an x-ray beam z-axis profile using the detector array, and determine an adjustment to the position of the x-ray source based on the determined x-ray beam z-axis profile.

In another embodiment, an imaging system is provided. The imaging system includes a multislice detector array having at least two rows of detector cells displaced along a z-axis, an x-ray source for radiating an x-ray beam toward the detector array, and a computer coupled to the detector array and the x-ray source, wherein the computer is programmed to determine an x-ray beam z-axis profile using the detector array, and determine a position adjustment of the x-ray source using the determined x-ray beam z-axis profile.

In yet another embodiment, a method for aligning an x-ray source in an imaging system is provided. The imaging system includes a multislice detector array having a plurality of rows of detector cells displaced along a z-axis and an x-ray source for radiating an x-ray beam toward the detector array. The method includes determining an x-ray beam z-axis profile using the detector array, and determining an adjustment to the position of the x-ray source using the determined x-ray beam z-axis profile.

DETAILED DESCRIPTION OF THE INVENTION

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 1:
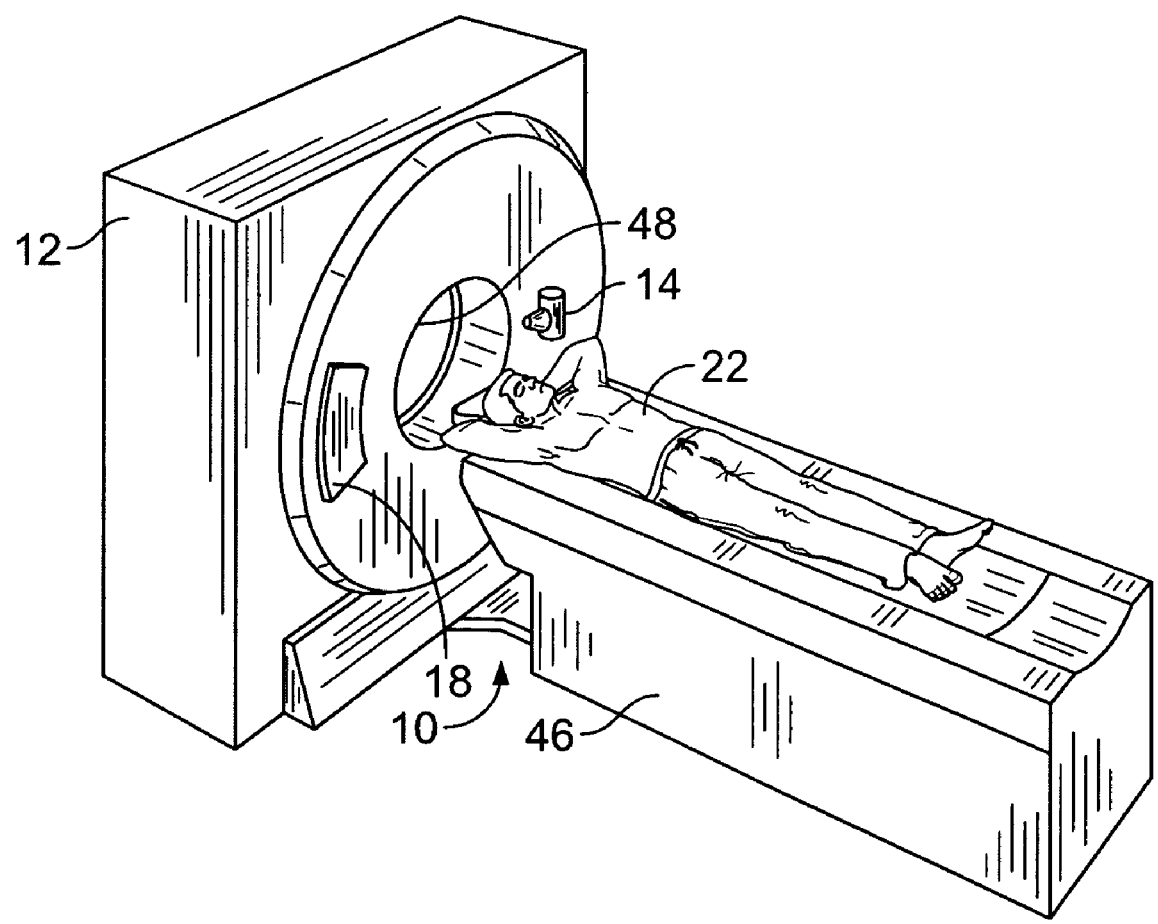
FIG. 1 is a pictorial view of a multi slice volumetric CT imaging system.
Figure 2:
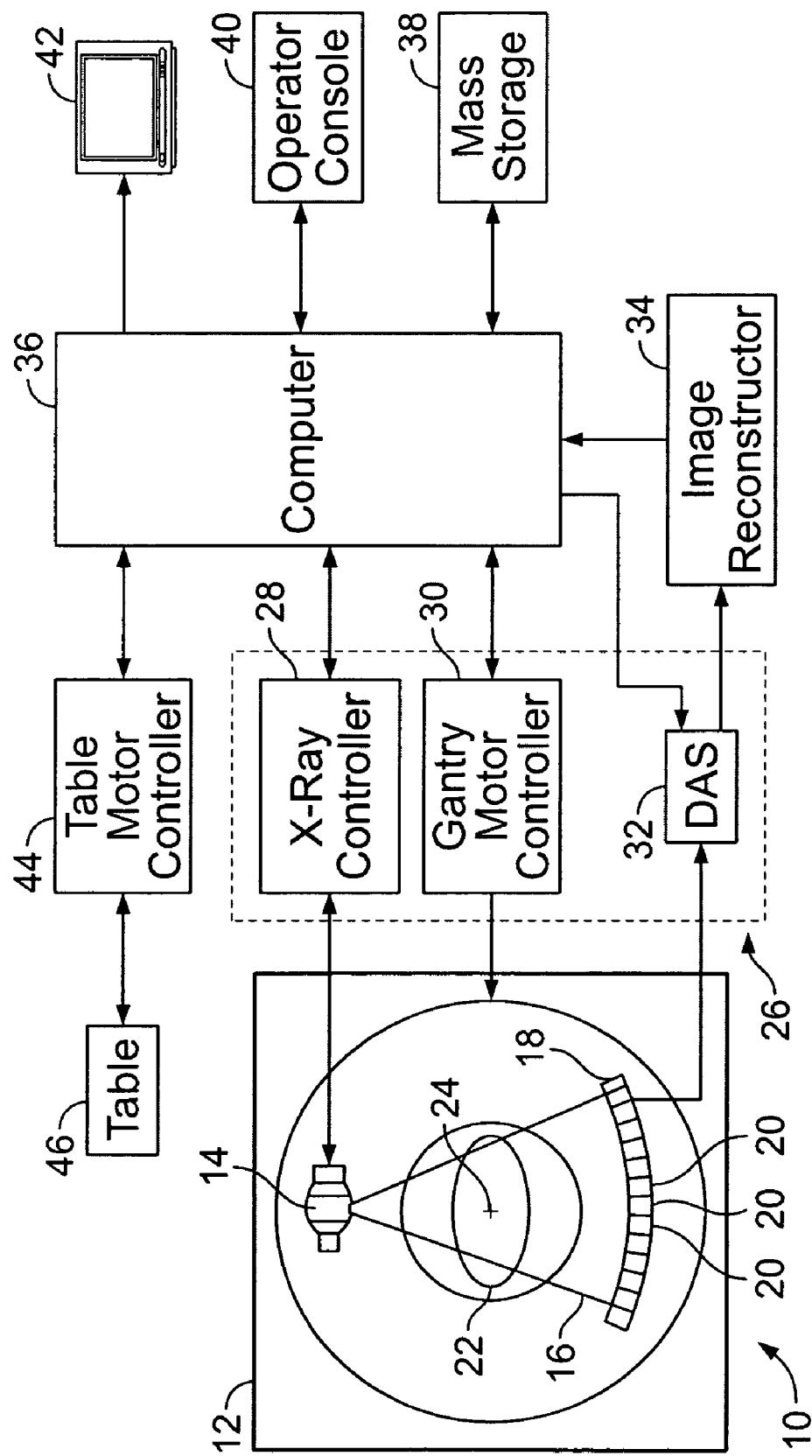
FIG. 2 is a block schematic diagram of the multi slice volumetric CT imaging system illustrated in FIG. 1.

FIG. 1 is a pictorial view of a multi slice volumetric CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of x-rays toward a detector array 18 on the opposite side of gantry 12.

Detector array 18 is formed by a plurality of detector rows (not shown) including a plurality of detector elements 20, which together sense the projected x-ray beams that pass through an object, such as a medical patient 22. Each detector element 20 produces an electrical signal that represents the intensity of an impinging radiation beam and hence the attenuation of the beam as it passes through patient 22. An imaging system 10 having a multislice detector array 18 is capable of providing a plurality of images representative of patient 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about an axis of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36, which stores the image in a mass storage device 38.

Computer 36 also receives commands and scanning parameters from an operator via console 40 that has a keyboard. An associated display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 that controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Set forth below is a description of an exemplary multislice CT system in accordance with one embodiment of the present invention. Although one embodiment of the system is described in detail below, it should be understood that many alternative embodiments of the inventions are possible. For example, although one particular detector and one particular pre-patient collimator are described, other detectors or collimators could be used in connection with the system, and the present invention is not limited to practice with any one particular type of detector. Specifically, the detector described below includes a plurality of modules and each module includes a plurality of detector cells. Rather than the specific detector described below, a detector which has non-segmented cells along the z-axis, and/or a detector which has multiple modules with multiple elements along the x-axis and/or z-axis joined together in either direction to acquire multislice scan data simultaneously, can be utilized. Generally, the system is operable in a multislice mode to collect one or more slices of data. Axial and helical scans can be performed with the system, and cross section images of a scanned object can be processed, reconstructed, displayed, and/or archived.

Figure 3:
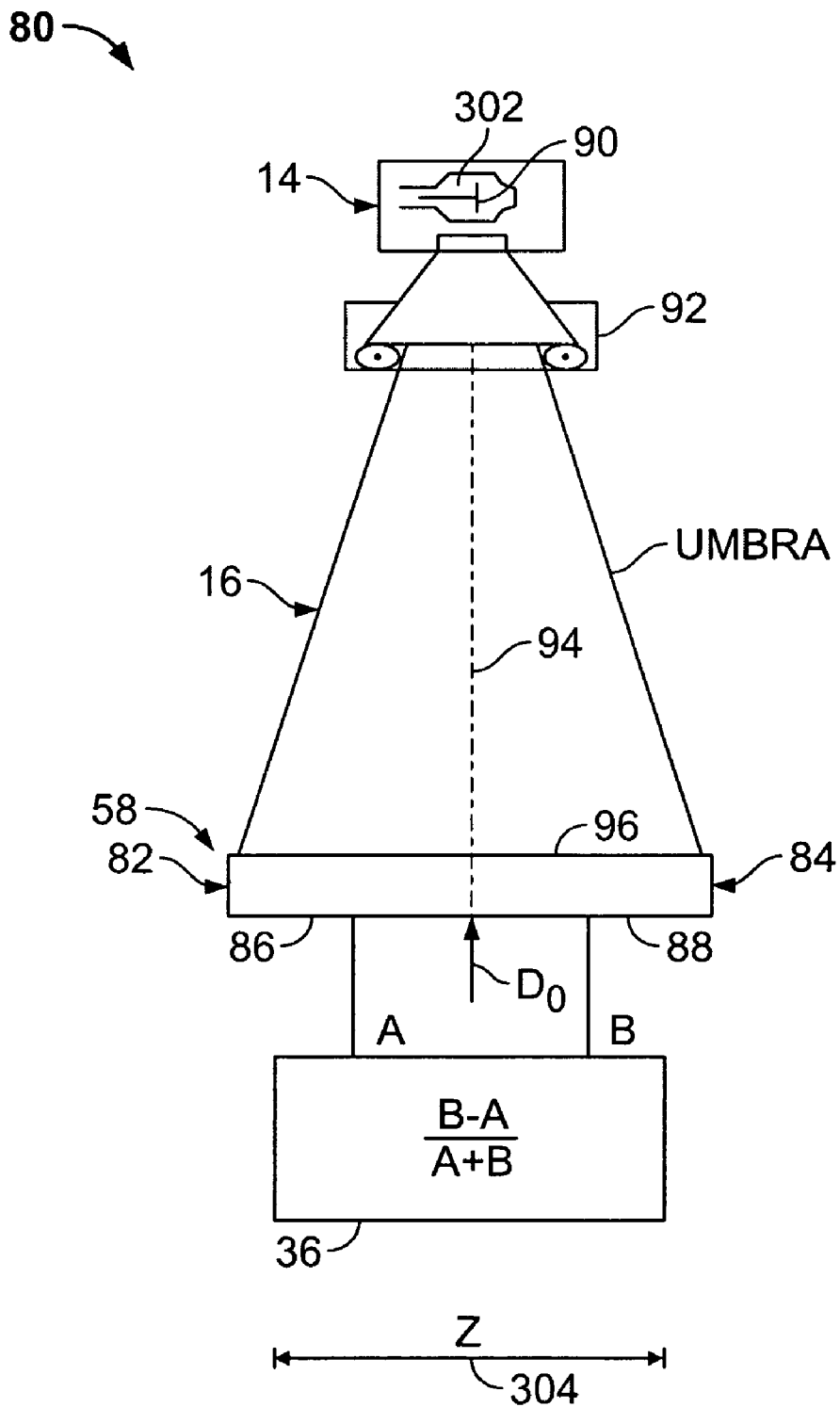
FIG. 3 is a schematic side view of an exemplary embodiment of a detector array position determination system.

FIG. 3 is a schematic side view of an exemplary embodiment of a detector array position determination system 80. System 80 may be used to determine a detector misalignment $(Z_d)$ distance after an x-ray tube 302 of radiation source 14 is replaced. System 80 is a "two slice" system that includes a first row 82 of detector cells and a second row 84 of detector cells that are utilized to obtain projection data. Detector cells 86 and 88, in addition to obtaining projection data, are utilized for determining a position of detector array 18 along a z-axis 304.

More specifically, and as shown in FIG. 3, x-ray beam 16 emanates from a focal spot 90 of radiation source 14 (shown in FIG. 2). X-ray beam 16 is collimated by a pre-patient collimator 92, and collimated x-ray beam 16 is projected toward detector cells 86 and 88. A plane 94, generally referred to as the "fan beam plane", contains the centerline of focal spot 90 and the centerline of x-ray beam 16. In FIG.

3, fan beam plane 94 is aligned with the centerline $D_0$ of exposure area 96 on detector cells 86 and 88.

The signal intensity A of the signal output by detector cell 86 and the signal intensity B of the signal output by detector cell 88 are related to the z-axis profile of x-ray beam 16 and the position of detector array 18. Specifically, the x-ray beam z-axis profile and the position of centerline of detector array 18 are determined by relating the signal intensities A and B according to the ratio [(B−A)/(A+B)]. Such ratio can be determined by computer 36 (FIG. 2). Assuming a uniform x-ray beam 16 and response of detector array 18, umbra of x-ray beam 16 is centered over detector array 18 when signal intensity A is equal to signal intensity B.

The position of detector array 18 may be offset to correct for movement of x-ray beam 16. Detector array 18 is typically aligned when radiation source 14 is operating at an ambient, or room temperature. A typical operating temperature of radiation source 14 may be within the range of 50% to 100% of the maximum operating temperature. Accordingly, thermal drift may cause the movement of the focal spot position. To compensate for the thermal drift of x-ray beam 16, the position of detector array 18 may be adjusted, or offset from centerline of x-ray beam 16 by a z-axis correction factor. In one embodiment, the position of detector array 18 is adjusted until the centerline of detector array 18 is offset from the x-ray beam centerline 94 by the z-axis correction factor. Specifically, the z-axis position of detector array 18 may be adjusted until:

Z-axis correction factor=($S*[(B−A)/(A+B)]$), where

S is a scale factor and is dependent on the shape of x-ray beam 16.

For example, where S has been determined to be 4.7 and for a center adjustment point detector array channel, respective signal intensities A=40 and B=60, the determined z-axis position of detector array 18 is (4.7*[(60−40)/(40+60)])=0.94 mm. If the z-axis correction factor for correction of thermal drift of x-ray beam 16 is −1.0 mm, the position of detector array should be altered by 1.94 mm, i.e., the distance between −1.0 mm and 0.94 mm. Specifically, the position of detector array 18 must be adjusted so that the intensity of signal B is reduced. This is accomplished by adjustment of detector array 18 so that the intensity of signal A becomes larger with respect to the intensity of signal B. For example, if position of detector array 18 is adjusted so that the intensity of signal B is 39 and the intensity of signal A is 61, position of detector array 18 would be approximately −1.0 mm. Specifically, (4.7*[39−61)/(61+39)])−1.0 mm. Therefore, detector array 18 is properly adjusted.

In a similar manner, each adjustment point of detector array 18 is adjusted so that entire detector array 18 is properly positioned. Specifically, in one embodiment, the z-axis position of detector array 18 is determined for a left, center and right adjustment point (not shown) by collecting signal intensities from at least one channel surrounding each adjustment point. In another embodiment, signal intensities from a plurality of channels surrounding each adjustment point may be used to determine z-axis position of detector array 18. Specifically, for example, the signal intensities may be averaged to determine the z-axis position of detector array 18. In addition, the z-axis correction factor may compensate, or correct for movement of other components as well as collimation and alignment tolerances.

By using the above-described ratio and correction factor, a detector array position may be determined without requiring separate alignment tools. Knowing the detector array position with respect to fan beam plane 94 permits determining other CT imaging system dimensional parameters that may be used for alignment of, for example, x-ray tube 302.

Figure 4:
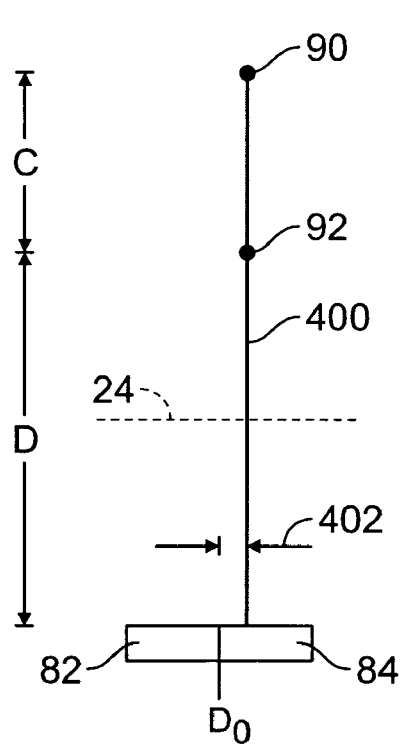
FIG. 4 is a schematic side view of a portion of the multislice volumetric CT imaging system shown in FIG. 1.

FIG. 4 is a schematic side view of a portion of multislice volumetric CT imaging system 10 (shown in FIG. 1). In the exemplary embodiment, a centerline 400 of fan beam plane 94 intersects detector cell 84 at a point offset from centerline $D_0$ by a distance 402. Distance 402 may represent a z-axis correction factor to compensate for thermal drift. Distance 402 also may represent an amount of misalignment of detector array 18. Calibration and alignment procedures are used to ensure focal point 90 and collimator 92 are maintained in substantial alignment. During operation of system 10, centerline 400 is substantially perpendicular to axis of rotation 24 when focal point 90 and collimator 92 are in substantial alignment.

Figure 5:
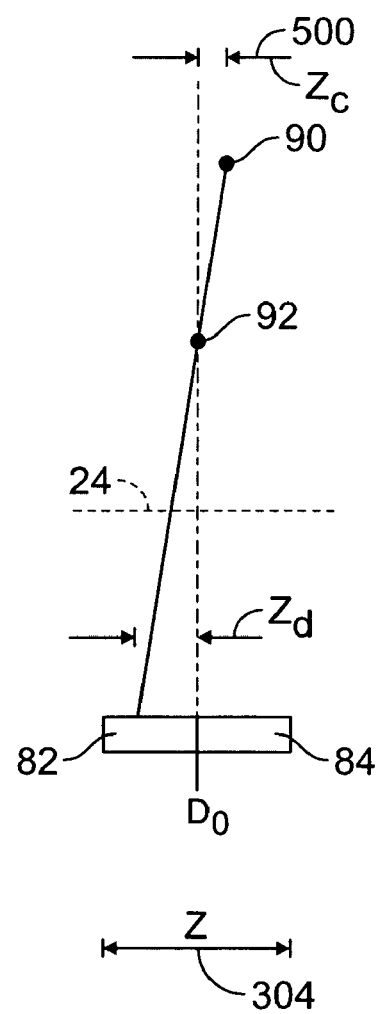
FIG. 5 is a schematic side view of a portion of the multislice volumetric CT imaging system shown in FIG. 1.

FIG. 5 is a schematic side view of a portion of multislice volumetric CT imaging system 10 (shown in FIG. 1). In the exemplary embodiment, focal point 90 is misaligned with respect to collimator 92 due to, for example, an x-ray source tube being replaced. A tube misalignment distance $Z_c$ 500 may be determined using the relationship:

$Z_c = Z_d(C/D)$, where $Z_d$ is an apparent detector misalignment due to misalignment of the tube, C is an x-ray path length between the focal point of the tube and the collimator, and D is an x-ray path length from the collimator to the detector.

$Z_d$ may be determined using the methods described above. C and D are values known from accurate new build fabrication specifications. Once $Z_c$ is determined, the replaced x-ray source tube may be repositioned by an amount equal to $Z_c$. Although alignment of the x-ray source tube may be performed manually, it is also completplated that the x-ray source tube may also be repositioned using a positioning device either during an off-line period or dynamically during operation.

The above-described embodiments of an imaging system provide a cost-effective and reliable means for maintaining alignment of a radiation source in an imaging system. More specifically, parameters having known values and parameters having values that may be determined without using auxiliary equipment or measuring devices are used to determine an amount of tube misalignment in the imaging system. As a result, the described methods of determining misalignment of the x-ray source tube facilitates maintenance and availability of the CT imaging system in a cost-effective and reliable manner.

Exemplary embodiments of imaging system methods and apparatus are described above in detail. The imaging system components illustrated are not limited to the specific embodiments described herein, but rather, components of each imaging system may be utilized independently and separately from other components described herein. For example, the imaging system components described above may also be used in combination with different imaging systems. A technical effect of the various embodiments of the systems and methods described herein include at least one of facilitating radiation source alignment in the imaging system.

While the invention has been described in terms of various specific embodiments, those skilled in the art will recognize that the invention can be practiced with modification within the spirit and scope of the claims.

What is claimed is:

1. A system for aligning an x-ray source position in an imaging system, the imaging system including a multislice detector array having a plurality of rows of detector cells displaced along a z-axis and an x-ray source for radiating an x-ray beam toward the detector array, said system configured to:
   determine an x-ray beam z-axis profile using the detector array; and
   determine an adjustment to the position of the x-ray source based on the determined x-ray beam z-axis profile.

2. A system in accordance with claim 1 wherein said system is configured to determine an x-ray beam umbra center.

3. A system in accordance with claim 1 wherein said system is configured to:
   obtain separate signals from at least a first detector cell in a first detector cell row and a second detector cell in a second detector cell row of the detector array; and
   determine the x-ray beam umbra position from the intensities of the separate signals.

4. A system in accordance with claim 2 wherein said system is configured to determine an offset of the detector array position from the x-ray beam umbra center position by a z-axis correction factor.

5. A system in accordance with claim 4 wherein said system is configured to determine a tube misalignment using the z-axis correction factor.

6. A system in accordance with claim 5 wherein said system is configured to determine a tube misalignment using the relationship:

$$Z_c = Z_d(C/D), \text{ where}$$

$Z_d$ is an apparent detector misalignment due to misalignment of the tube,
C is an x-ray path length between the focal point of the tube and the collimator, and
D is an x-ray path length from the collimator to the detector.

7. An imaging system comprising a multislice detector array having at least two rows of detector cells displaced along a z-axis, an x-ray source for radiating an x-ray beam toward the detector array, and a computer coupled to said detector array and said x-ray source, said computer programmed to:
   determine an x-ray beam z-axis profile using said detector array; and
   determine a position adjustment of said x-ray source using the determined x-ray beam z-axis profile.

8. A system in accordance with claim 7 wherein said system is configured to determine an x-ray beam umbra position.

9. A system in accordance with claim 7 wherein said system is configured to determine an x-ray beam umbra center.

10. A system in accordance with claim 7 wherein said system is configured to:
   obtain separate signals from at least a first detector cell in a first detector cell row and a second detector cell in a second detector cell row of the detector array; and
   determine the x-ray beam umbra position wherein the signal from the first detector cell has an intensity A and the signal from the second detector cell has an intensity of B, and said system is configured to determine the x-ray beam umbra position from the intensities A and B using the relationship [(B−A)/(A+B)].

11. A system in accordance with claim 10 wherein said system is configured to determine a position of the detector array using the relationship:

$$\text{z-axis correction factor} = (S*[(B-A)/(A+B)]), \text{ where:}$$

S represents a z-axis distance scale factor.

12. A system in accordance with claim 11 wherein said system is configured to determine an offset of the detector array position from the x-ray beam umbra center position by a z-axis correction factor.

13. A system in accordance with claim 12 wherein said system is configured to determine a tube misalignment using the z-axis correction factor.

14. A system in accordance with claim 13 wherein said system is configured to determine a tube misalignment using the relationship:

$$Z_c = Z_d(C/D), \text{ where}$$

$Z_d$ is an apparent detector misalignment due to misalignment of the tube,
C is an x-ray path length between the focal point of the tube and the collimator, and
D is an x-ray path length from the collimator to the detector.

15. A method for aligning an x-ray source in an imaging system, the imaging system including a multislice detector array having a plurality of rows of detector cells displaced along a z-axis and an x-ray source for radiating an x-ray beam toward the detector array, said method comprising:
   determining an x-ray beam z-axis profile using the detector array; and
   determining an adjustment to the position of the x-ray source using the determined x-ray beam z-axis profile.

16. A method in accordance with claim 15 wherein determining an x-ray beam z-axis profile comprises determining an x-ray beam umbra position.

17. A method in accordance with claim 16 wherein determining the x-ray beam umbra position comprises the step of determining an x-ray beam umbra center.

18. A method in accordance with claim 16 wherein determining an x-ray beam z-axis profile comprises:
   obtaining separate signals from at least a first detector cell in a first detector cell row and a second detector cell in a second detector cell row of the detector array; and
   determining the x-ray beam umbra position from the intensities of the separate signals.

19. A method in accordance with claim 18 wherein the signal from the first detector cell has an intensity A and the signal from the second detector cell has an intensity of B, and determining x-ray beam umbra position from the intensities A and B is performed using the relationship [(B−A)/(A+B)].

20. A method in accordance with claim 19 wherein determining a position of the detector array is performed using the relationship:

$$\text{z-axis correction factor} = (S*[(B-A)/(A+B)]), \text{ where:}$$

S=a z-axis distance scale factor.

21. A method in accordance with claim 15 wherein adjusting position of the x-ray source comprises determining an offset of the detector array position from the x-ray beam umbra center position by a z-axis correction factor.

22. A method in accordance with claim 15 wherein adjusting the position of the x-ray source using the determined x-ray beam z-axis profile comprises determining a tube misalignment using the z-axis correction factor.

23. A method in accordance with claim 22 wherein determining a tube misalignment using the z-axis correction factor comprises determining a tube misalignment using the relationship:

$Z_c = Z_d(C/D)$, where $Z_d$ is an apparent detector misalignment due to misalignment of the tube, C is an x-ray path length between the focal point of the tube and the collimator, and D is an x-ray path length from the collimator to the detector.

* * * * *